Figure 1:
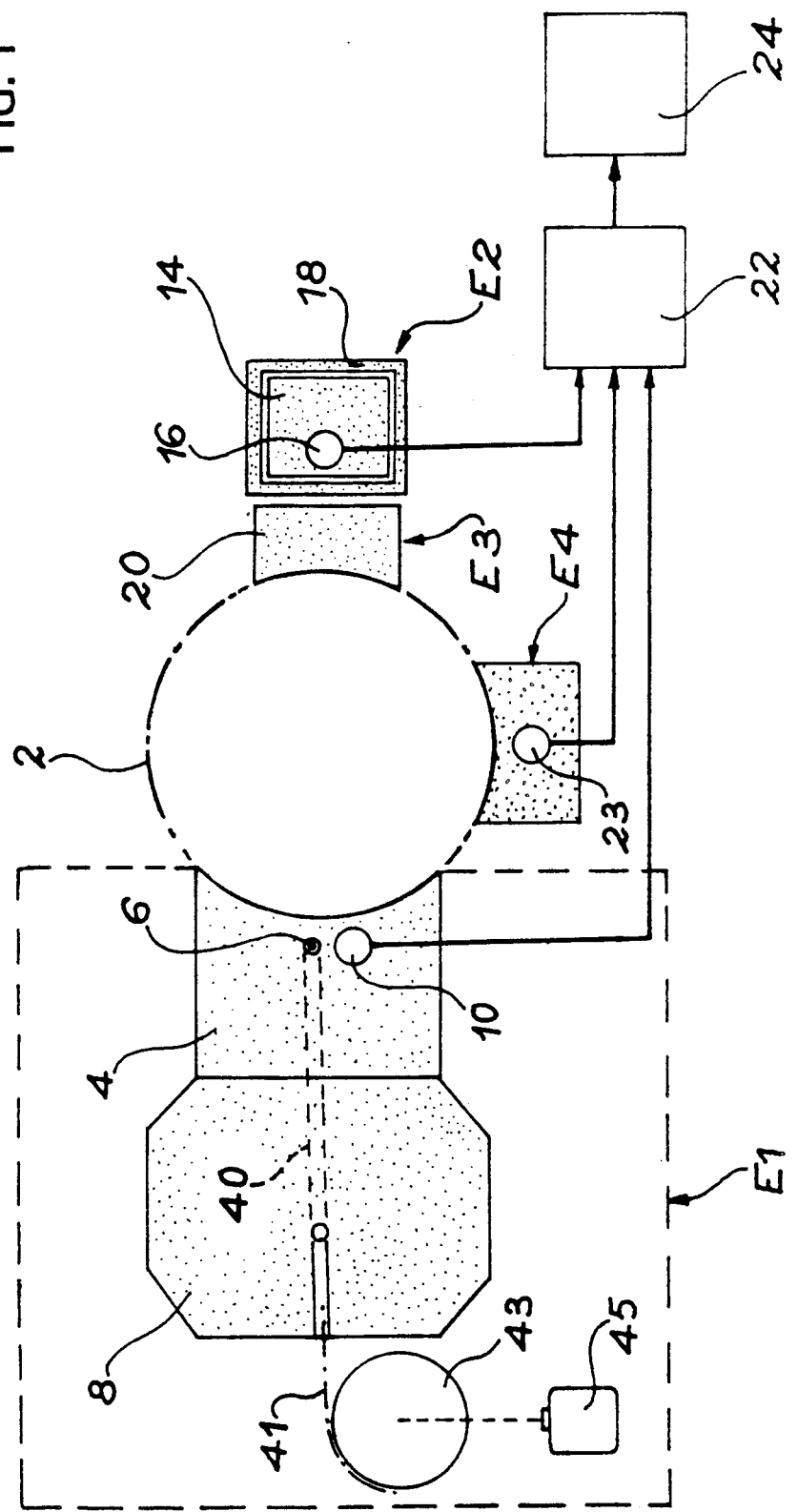

United States Patent [19]

Bernard et al.

[11] Patent Number: 5,002,721

[45] Date of Patent: Mar. 26, 1991

[54] APPARATUS FOR DETERMINING NUMBER OF NEUTRONS EMITTED BY FISSILE MATERIAL DURING INDUCED FISSILE

[75] Inventors: Patrice Bernard, Venelles; Jean Cloue, Manosque; Pinel Jacques, Beaumont De Pertuis; Jacques Romeyer-Dherbey, Aix en Provence, all of France

[73] Assignee: Commissariat a l'Energie Atomique, Paris, France

[21] Appl. No.: 552,336

[22] Filed: Jul. 12, 1990

Related U.S. Application Data

[63] Continuation of Ser. No. 241,405, Sep. 7, 1988, abandoned.

[30] Foreign Application Priority Data

Sep. 8, 1977 [FR] France ............... 87 12423

[51] Int. Cl.⁵ .............. G21G 1/06; G01T 3/00
[52] U.S. Cl. .................... 376/159; 376/257
[58] Field of Search .......... 376/159, 157, 257

[56] References Cited

U.S. PATENT DOCUMENTS

| | | |
|---|---|---|
| 2,936,274 | 5/1960 | Dessauer ............... 376/159 |
| 2,969,307 | 1/1961 | Fermi et al. ........... 376/159 |
| 2,983,817 | 5/1961 | Earley et al. .......... 376/159 |
| 3,008,047 | 11/1961 | Earley et al. ......... 376/159 |
| 3,018,374 | 1/1962 | Pritchett ............... 376/159 |
| 3,222,521 | 12/1965 | Einfeld et al. . | 
| 3,499,151 | 3/1970 | Mayer ................... 376/159 |
| 3,699,338 | 10/1972 | Baumann et al. ...... 376/159 |
| 3,707,631 | 12/1972 | Untermyer ............ 376/159 |
| 3,786,256 | 1/1974 | Untermyer ............ 376/159 |
| 3,832,545 | 8/1974 | Bartko .................. 376/159 |
| 4,043,755 | 8/1977 | Bartko et al. ......... 376/159 |
| 4,266,132 | 3/1981 | Marshall .............. 376/159 |
| 4,464,330 | 8/1984 | Speir et al. .......... 376/159 |
| 4,497,768 | 2/1985 | Caldwell et al. ..... 376/157 |
| 4,647,420 | 3/1987 | Bramblett et al. ... 376/159 |
| 4,682,043 | 7/1987 | Marshall . | |
| 4,717,466 | 10/1986 | Menlove et al. . | |

FOREIGN PATENT DOCUMENTS 2613700 10/1977 Fed. Rep. of Germany ...... 376/159
58-211682 9/1983 Japan .

OTHER PUBLICATIONS

Nuclear Instruments & Methods, vol. 220, Nos. 2,3, Mar. 1984, Close et al., pp. 531–536.
Nuclear Technology, vol. 10, Mar. 1971, pp. 366–379, Menlove et al.

Primary Examiner—Harvey E. Behrend
Attorney, Agent, or Firm—Michael N. Meller

[57] ABSTRACT

It comprises a first assembly (E1) constituted by a neutron radiation source (6), a hydrogenated material block (4) having a recess for receiving said source (6) and a first neutron detector (10); a second assembly (E2) constituted by a hydrogenated material block (14) surrounded by a material stopping the thermal neutrons (18) and a second neutron detector (16) placed in the hydrogenated material block (14); the first assembly (E1) and the second assembly (E2) being placed on either side of the area to be controlled (2). A foldback protective casket (8) can receive the neutron radiation source (6).

6 Claims, 4 Drawing Sheets

APPARATUS FOR DETERMINING NUMBER OF NEUTRONS EMITTED BY FISSILE MATERIAL DURING INDUCED FISSILE

This application is a continuation of application Ser. No. 241,405, filed 9/7/88, now abandoned.

DESCRIPTION

The present invention relates to an apparatus for controlling the criticality of nuclear material.

In nuclear installations it is necessary to control the absence of criticality risks due to an accumulation of fissile materials, which could lead to a divergent chain reaction. It can also be necessary to quantitatively measure the fissile material content.

Apparatuses are already known which use passive methods for solving these problems. These methods are based on the detection of natural neutron radiation resulting from spontaneous fissions or interactions of alpha particles with light elements also producing neutrons.

Other methods based on the detection of spontaneous gamma radiation are also used and sometimes associated with methods using neutron counting.

However, there are certain limitations to these methods. It is necessary to know the isotopic composition of the heavy nuclei in the area to be controlled. Moreover, these methods cannot be used on uranium cycles, because they do not give significant results.

The present invention relates to a criticality control and fissile material concentration measuring apparatus obviating these disadvantages and which in particular is based on an active neutron interrogation process making it possible to induce nuclear reactions, which are then analyzed in order to quantitatively determine the radioelement content of the nuclear waste.

The present invention therefore relates to an apparatus for the criticality control and the measurement of the concentration of fissile material by active neutron interrogation, said fissile material being contained in an area to be controlled, characterized in that it comprises a first assembly constituted by a neutron radiation source, a block of hydrogenated material having a recess for receiving said source and a first neutron detector; a second assembly constituted by a hydrogenated material block surrounded by a thermal neutron stopping material and a second neutron detector placed in said hydrogenated material block; whereby said first assembly and said second assembly are placed on either side of the area to be controlled.

Preferably, the first assembly also has a foldback protective casket able to receive the neutron radiation source and a means for transferring said neutron radiation source from the hydrogenated material block to the foldback casket and vice versa.

Finally, in certain cases, it could be necessary to use a third hydrogenated material block, which is placed between the area to be controlled and said second assembly.

As a result of these features, a control apparatus is obtained making it possible to obtain a non-intrusive and non-destructive measurement and which supplies an information directly representing the fissile material in the area to be controlled and which is significant with respect to the gain and the fissile material content.

Other features and advantages of the invention are described in greater detail hereinafter with respect to a non-limitative embodiment and the attached drawings, wherein show:

FIG. 1 An overall view of a fissile material criticality control apparatus according to the invention.

Figure 2:
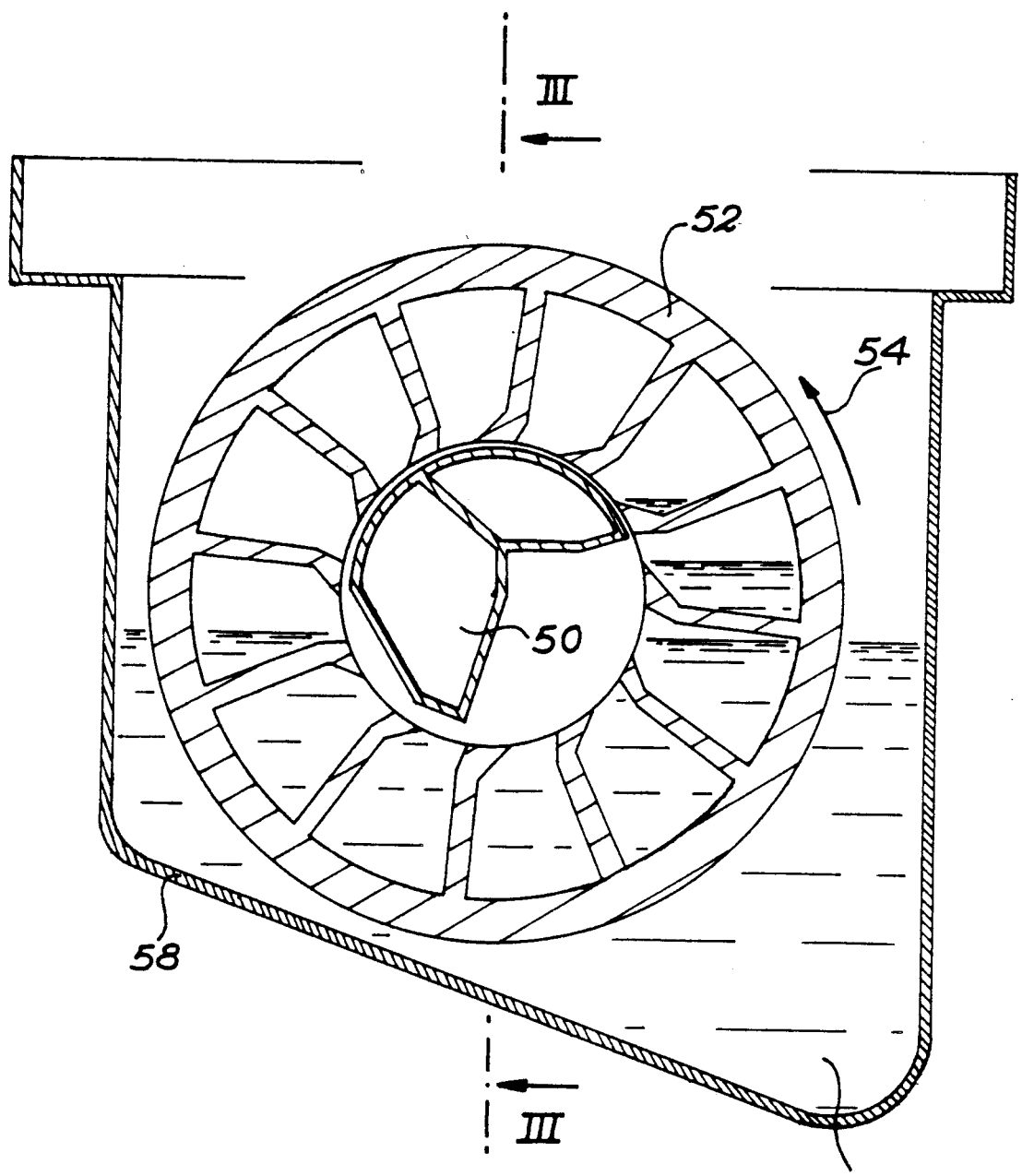

FIG. 2 A diagram of a dissolver for the reprocessing of irradiated nuclear fuel.

Figure 3:
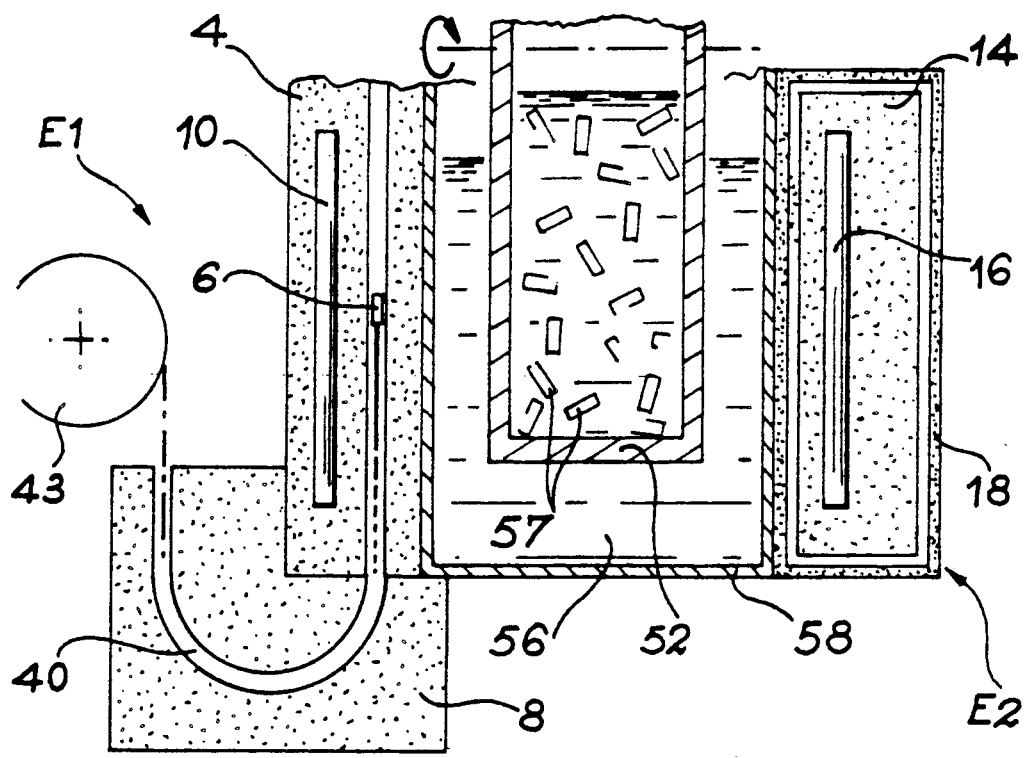

FIG. 3 An example of an application of a fissile material criticality control apparatus according to the invention to the dissolver of FIG. 2.

Figure 4:
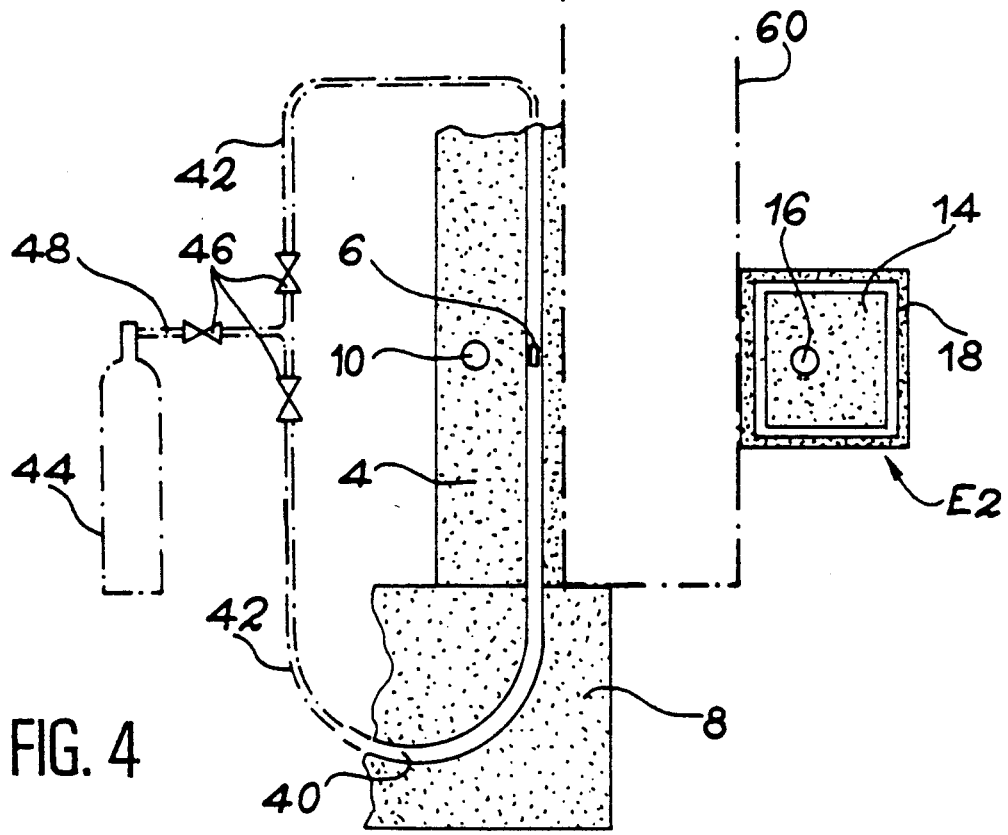

FIG. 4 Another example of applying the criticality control apparatus according to the invention to the measurement of the gain in a fuel assembly under water.

FIGS. 5a to 5e The processing of the signals from the detectors.

FIG. 1 is an overall view of a fissile material criticality control apparatus according to the invention, in which 2 is an area to be controlled. This area contains fissile materials in solid form, e.g. fuel assemblies, fuel rods or pellets in the form of dispersed solids, such as e.g. portions of sheared fuel needles, or also in liquid form (nuclear materials in dissolved form, e.g. acids) and in the form of deposits (mud, pulverulent deposits).

It is therefore necessary to check for the absence of a criticality risk, which would be due to the accumulation of fissile materials under physical and geometrical conditions such that the gain k would exceed 1 and a divergent chain reaction could occur. It is also necessary to quantitatively measure the content and/or concentration of fissile materials in the area to be controlled 2. The apparatus according to the invention permits the criticality control and the fissile material concentration measurement. This apparatus essentially comprises four assemblies E1, E2, E3 and E4.

The first assembly E1 is constituted by a hydrogenated material block, e.g. of type $CH_2$. A recess is made in the block for receiving a fast neutron source 6. For example, said source is an $Am^{241}$-Be or $Cf^{252}$ source. In addition, the foldback protective casket 8 is located in the vicinity of block 4 and is also constituted by a hydrogenated material block. The assembly E1 has transfer means making it possible to pass the source from the recess of block 4 (irradiation position) to the foldback protective casket (foldback or storage position) and then return the source 6 to the irradiation position. This transfer lasts approximately a half second. Preferably, these transfer means are constituted by a guide tube 40 connected at one of its ends to the hydrogenated material block 4 and at its other end to the foldback protective casket 8. The guide tube 40 partly traverses the block 4 and the casket 8. A flexible cable 41 is fixed by one of its ends to a rotary drum 43 and by its other end to source 6. Drum 43 is rotated by means of a motor, e.g. a stepping motor 45, whose rotation in one direction makes it possible to introduce the source into block 4 and its rotation in the other direction to remove source 6 from block 4 in order to bring it into the foldback position in casket 8.

According to another embodiment, the means for introducing the source into the irradiation position and for returning same to the storage position are of a pneumatic nature. They comprise a guide tube 40 with a sufficiently large internal cross-section to permit the passage of the source. At one of its ends, said guide tube 40 issues into the hydrogenated material block 4 and at its other end it is connected to the protective casket 8. Moreover, a tube 42 with a smaller cross-section than guide tube 40, in such a way that source 6 cannot penetrate the said tube, has ends issuing in front of the ends of guide tube 40. Tube 42 is connected to a compressed gas source 44, e.g. a compressed air cylinder. Various valves 46 placed on tube 42 and on tube 48 connecting tube 42 to the compressed gas cylinder 44 make it possible to pneumatically propel the source 6 with a very considerable speed for introducing it into the hydrogenated material block in the irradiation position of the zone to be controlled or for returning it to the protective casket 8.

Moreover, assembly E1 comprises a neutron detector 10, e.g. constituted by a fission chamber or a type $He^3$ detector. Detector 10 is placed alongside the neutron source 6 within the hydrogenated material 4. The detector can be placed in the area to be controlled or outside said area.

Furthermore, the criticality control apparatus has a second assembly E2 constituted by a second hydrogenated material block 14, e.g. of the $CH_2$ type and in which is placed a neutron detector 16 of the fission chamber or $He^3$ detector type. The hydrogenated material block 14 is surrounded by a material 18, which strongly absorbs thermal neutrons, e.g. boron carbide and/or cadmium.

Assembly E2 is positioned opposite to assembly E1 with respect to the assembly to be controlled. Thus and as can be seen in FIG. 1, assemblies E1 and E2 are diametrically opposite. They are separated by all or part of the area to be controlled. In the case where they are only separated by part of the area to be controlled, it is obvious that the assemblies E1 and E2 must be mobile with respect to the area to be controlled, or conversely the area to be controlled must be displaceable with respect to the assemblies E1 and E2 which remain fixed, in such a way that all said zone is controlled.

The position of the foldback or storage casket 8 with respect to the area to be controlled 2 and the remainder of the measuring apparatus, as well as the thickness of the casket wall are such that the influence of source 6, when it is in the foldback position inside the casket on the signal of the neutron detectors 10 and 16, as well as the fissile material contained in the area to be controlled, is of a negligible nature.

The criticality control apparatus also has a third assembly E3, whose use is optional. This third assembly E3 is constituted by a third hydrogenated material block 20, e.g. of type $CH_2$ and which is placed between the area to be controlled 2 and assembly E2.

Finally, the control apparatus according to the invention can have at least one fourth assembly E4 constituted by a hydrogenated material block 21 in which is placed a third detector 23. Detector 23 makes it possible to obtain a higher delayed neutron detection efficiency, particularly if the fissile material is remote from detector 10.

The operating principle of this apparatus is as follows. When the neutron source 6 is in the irradiation position, the fast neutrons emitted by said source slow down in the area to be controlled, because the latter contains hydrogenated materials. The fast neutrons induce fissions on the fissile nuclei contained in the area to be controlled 2. Fast neutrons are reemitted during said fissions and cause new chain fissions. These neutrons are detected by neutron detector 16. The counting rate detected by the neutron detector is a function of the multiplication factor k of the area to be controlled. Thus, the average distance covered by the fast neutrons, having an energy of approximately 2 MeV, before being absorbed and causing new fissions, is approximately 15 cm. However, according to the invention, the distance between the neutron source 6 and the detector 16 which is diametrically opposite to said source with respect to the area to be controlled is chosen in such a way that the thickness of hydrogenated material contained in the area to be controlled 2 exceeds approximately 30 cm of liquid water equivalent. In the case where the area to be controlled does not contain enough hydrogenated material, the hydrogenated material block 20 having a matched thickness is added, so that the hydrogenated material thickness between the source and the detector becomes equal to or greater than approximately 30 cm of liquid water equivalent. As a result of this arrangement, the fast neutrons emitted by source 6 cannot reach the detector 16, in such a way that only the neutrons coming from new fissions with neutron reemission are detected by detector 16 (the characteristic decay distance of the fast neutron flux of the neutrons reemitted being approximately 4.8 cm). The higher the multiplication factor k, the more fast neutrons emitted during the induced fissions are detected by detector 16.

The useful signal $Su_2$ of detector 16 due to the neutrons emitted during the fissions induced by the neutrons of source S is expressed by the formula:

$$Su_2 = CS \frac{k}{1-k}$$

in which S is the intensity of the neutron source ($n.s^{-1}$), k is the multiplication factor of the area 2 to be controlled, C is a constant factor being a function of the geometry and the materials of the area to be controlled, the apparatus and the efficiency of detector 20. This constant factor is determined by calibration.

Moreover, assembly E2 is only sensitive to fast neutrons because the hydrogenated material block 14 is surrounded by a layer of a material, such as boron carbide or cadmium which highly absorb thermal neutrons. Thus, the thermal neutrons due to the neutrons emitted during the fissions induced by the neutrons of source 6 are stopped by layer 18. However, the fast neutrons pass through layer 18. They must then be thermalized, i.e. slowed down, in order that they can be detected by detector 16, which is the function of hydrogenated material 14. The signal emitted by detector 16 consequently represents the number of prompt neutrons. The knowledge of the useful signal of the detector 16, the intensity of the neutron source and the constant factor C consequently makes it possible to calculate k by means of the above formula.

However, when the nuclei contained in the area to be controlled are themselves fast neutron emitters, the signal emitted by the detector 16 due to these neutrons constitutes an undesired noise. In this case, the signal $S_2$ of detector 16 is measured on the one hand when source 6 is in the irradiation position and on the other when said source is in the foldback position in casket 8. By an appropriate signal processing method it is then possible to obtain the signal $Su_2$ representing the multiplication factor k and the fissile material content of the area to be controlled. The signal processing means e.g. comprise a subtracter circuit 22, which forms the difference between the signal emitted by detector 16 when source 6 is in the irradiation position and the signal emitted by said same detector when the source is in the foldback position. Moreover, an averaging circuit 24 establishes the average or mean of the differences calculated by the subtracter circuit during a given time period. Such signal processing means are known and will consequently not be described in further detail.

Finally, in situations where the signal due to parasitic neutrons is negligible, it is not necessary to move the source, which can then be fixed.

The apparatus according to the invention also makes it possible to detect delayed neutrons, i.e. neutrons emitted in a delayed manner by nuclides having decay periods between a few tenths of a second and a few dozen seconds.

Figure 5:
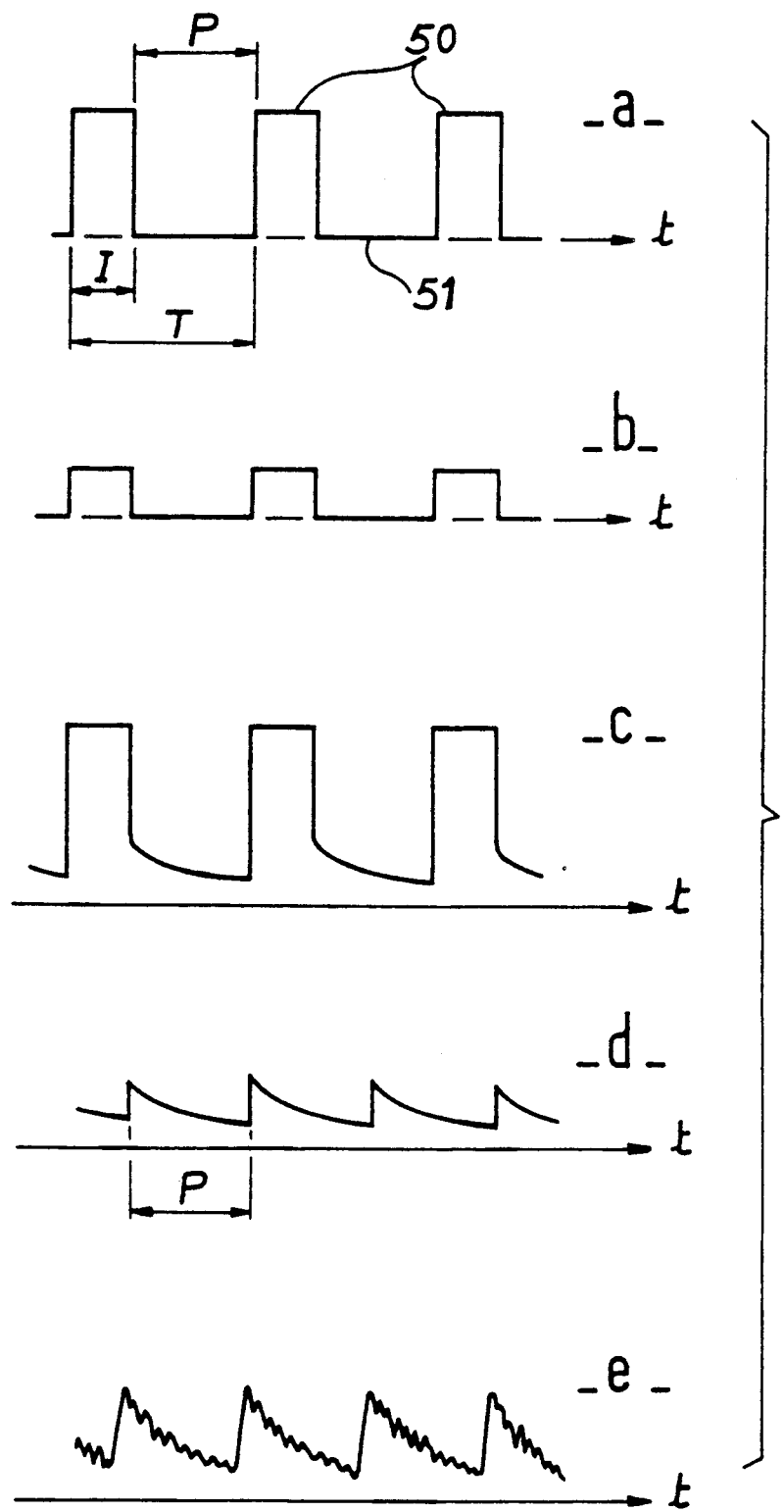

When source 6 is in the irradiation position, it induces fissions in the nuclei of atoms of fissile material contained in the area to be controlled. The source is removed to pass it into the foldback position and using detectors 10, 23 and possibly 16 the delayed neutrons emitted by the precursors formed by the induced fission are detected. The signal supplied by each of the detectors 10, 23 and possibly 16 is a function of the content of fissile nuclei and the number of delayed neutrons emitted by fission, said number depending on the type of fissile nuclei. The signals emitted by the detectors are then processed in order to calculate the number of delayed neutrons and deduce therefrom the content of fissile nuclei. FIG. 5 a is a chronogram relating to the presence/absence of the neutron source. Reference 50 designates the times when the neutron source 6 is in the irradiation position for a time I and reference 51 the times during which said source is removed into the foldback position for a time P. Irradiation and foldback are periodic of period $T = I + P$.

When the source is in the irradiation position (FIG. 5b), it induces a constant number of fissions in the fissile material present in the area to be controlled during time I. These fissions lead to the emission of prompt neutrons, which can be detected, in the manner explained hereinbefore, but also the emission of delayed neutrons appearing a few tenths of a second to a few dozen seconds after the withdrawal of the source. The number of neutrons and consequently the signal emitted by each of the detectors 10, 16 and 23 takes account of both the prompt neutrons and the delayed neutrons. This signal is consequently constant for time I and drops suddenly following the withdrawal of the source, which corresponds to the stoppage of the emission of prompt neutrons and then progressively decreases during a period of time, which corresponds to the delayed neutrons (FIG. 5c).

By an appropriate signal processing elimination takes place of period I corresponding to the prompt and delayed neutrons so as to only retain the period P corresponding to the delayed neutrons only.

FIG. 5d represents a theoretical curve and FIG. 5e a real signal taking account of undesired noise.

The signals received during period $P = T - I$ are averaged. On the result is then carried out a smoothing by least squares of an expression $G(t)$ of form $G(t) = Af(t) + B$, in which $f(t)$ is the characteristic form of emission of delayed neutrons as a result of an induced fission and $f(t)$ is a known function. A represents the gain and fissile material content and B is the undesired noise.

The combination of the result of the measurement of the number of prompt neutrons and the measurement of the number of delayed neutrons makes it possible to determine the fraction of $Pu^{239}$ in the fissile nuclei of the area to be controlled, the ratio of the number of delayed neutrons to the number of prompt neutrons emitted during fissions being substantially different in the case of plutonium 239 from that of the other fissile nuclei.

FIG. 2 is a diagram of a wheel-type dissolver for irradiated fuel reprocessing. It is known that the fuel needles or rods of a fast neutron or water nuclear reactor are constituted by a sheath containing $PuO_2$ and/or $UO_2$ pellets. When their life is ended, these needles are sheared into small portions 57, which arrive by a pipe 50 issuing into the centre of wheel 52, which rotates in the direction of arrow 54. It is constituted by a plurality, e.g. twelve buckets. It is partly immersed in a boiling, concentrated nitric acid bath 56 contained in the tank of dissolver 58. The nuclear material of the irradiated fuel is dissolved by the nitric acid before being led to a subsequent treatment.

It is necessary to ensure that during the filling of the bucket there is no criticality risk. For this purpose use is made of a detection apparatus according to the invention and as shown in FIG. 3, which is a sectional view along line III—III of the wheel of FIG. 2. On one side of the wheel (the left-hand side in FIG. 3), is provided an assembly E1 having a neutron source 6 and a neutron detector 10 in the vicinity of source 6. The detector and the source are both contained within a hydrogenated material block 4, as has been explained hereinbefore. A rectilinear, vertical guide tube makes it possible to clear the source for bringing same into the foldback position. The foldback or storage casket can be positioned above or below the irradiation position of the source. In the represented embodiment, the casket is located below the source. On the other side of the wheel there is an assembly E2 constituted by a neutron detector 16 embedded in a hydrogenated material block 14, which is itself surrounded by a layer 18 strongly absorbing thermal neutrons. It is obvious that in this embodiment, it would also be possible to have a third block, like block 20 described relative to FIG. 1 and whose function would be to increase the path of the neutrons within the hydrogenated material of the area to be controlled.

This apparatus consequently makes it possible to calculate the number of prompt neutrons and the number of delayed neutrons emitted by the fissile material contained in the bucket of wheel 52, when they pass between source 6 and detector 16, which is e.g. a $He^3$ tube. Through the measurement of the number of prompt neutrons, it is possible to determine the multiplication factor k and ensure that the latter is below the maximum permitted value (below 1). In addition, through the measurement of the number of delayed neutrons, it is possible to determine the content of fissile material in the different isotopes of the plutonium and uranium.

FIG. 4 shows a second example of applying a fissile material criticality control apparatus according to the invention. As in the example shown in FIG. 3, said apparatus comprises an assembly E1 located on one side of a fuel assembly 60 to be controlled and an assembly E2 diametrically opposite to assembly E1 with respect to assembly 60. In a conventional manner, assembly 60 is constituted by a bundle of fuel rods kept parallel to one another, e.g. by spacing grids mounted on a network of tie rods or guide tubes integral with end members. Said assembly 60 is maintained under water, so as to protect the operators against irradiation. Consequently, the control of said assembly must also take place under water and assemblies E1 and E2 are consequently immersed in the water of the storage pool of the assemblies. These assemblies are identical to those of the apparatus of FIG. 3, so that they will not be described again. Source 6 is also vertically mobile, which makes it possible to measure prompt neutrons and delayed neutrons. For example, the neutron detector can be tripled and the source system doubled for redundancy and reliability reasons. The source moves vertically, which makes it possible to control the assembly over its entire height. This also makes it possible to withdraw the source in the foldback position.

The criticality detection apparatus according to the invention consequently permits non-intrusive and non-destructive measurements. It provides an information directly representative of the fissile material in the controlled area and which is significant with respect to the multiplication and/or the fissile material content.

We claim:

1. An apparatus for determining the number of neutrons respectively emitted as the result of induced fissions in a fissile material during first and second predetermined time intervals, comprising:

first and second blocks of hydrogenated material arranged with said fissile material therebetween;

a neutron source displaceably arranged in said first block of hydrogenated material;

means for displacing said neutron source between first and second positions, said first position being sufficiently close to said fissile material that fissions are induced therein by neutrons emitted by said source, and said second position being sufficiently distant from said fissile material that a negligible number of fissions are induced therein by neutrons emitted by said source;

first neutron detecting means arranged inside said first block of hydrogenated material in proximity to said first position;

second neutron detecting means arranged inside said second block of hydrogenated material sufficiently distant from said first position that substantially no neutrons emitted by said source when in said first position reach said second neutron detecting means;

thermal neutron stopping means surrounding said second block of hydrogenated material; and processing means for processing the outputs of said first and second neutron detecting means during a first period of time when said source is maintained at said first position and during a second period of time when said source is maintained at said second position, said processing means utilizing said outputs to determine the number of prompt neutrons produced during said first time period and the number of delayed neutrons produced during said second time period as the result of fissions induced in said fissile material by neutrons emitted by said source during said first time period.

2. The apparatus as defined in claim 1, wherein said processing means comprises means for calculating a first value by subtracting the output of said second neutron detecting means when said source is in said second position from the output of said second neutron detecting means when said source is in said first position.

3. The apparatus as defined in claim 2, wherein said processing means further comprises means for calculating a second value by forming the ratio of said first value and a third value, said third value being in turn determined from the outputs of said first and second neutron detecting means immediately after said source has been moved from said first to said second position.

4. The apparatus as defined in claim 1, further comprising a third block of hydrogenated material in which said second position is located, said displacing means comprising a guide tube arranged in said first and third blocks of hydrogenated material, said guide tube extending between said first and second positions and having said source arranged therein.

5. The apparatus as defined in claim 1, further comprising a third block of hydrogenated material arranged between said fissile material and said second block of hydrogenated material.

6. The apparatus as defined in claim 1, further comprising a third block of hydrogenated material arranged on the periphery of said fissile material, and a third neutron detecting means located in said third block of hydrogenated material and coupled to said processing means.

* * * * *